US010806178B1

(12) United States Patent
He et al.

(10) Patent No.: US 10,806,178 B1
(45) Date of Patent: Oct. 20, 2020

(54) BIO-TRACEABLE ELECTRONIC CONSUMABLE DEVICE

(71) Applicant: Shenzhen Goodix Technology Co., Ltd., Shenzhen (CN)

(72) Inventors: Yi He, San Diego, CA (US); Bo Pi, San Diego, CA (US)

(73) Assignee: Shenzhen Goodix Technology Co., Ltd., Shenzhen (CN)

( * ) Notice: Subject to any disclaimer, the term of this patent is extended or adjusted under 35 U.S.C. 154(b) by 0 days.

(21) Appl. No.: 16/532,576

(22) Filed: Aug. 6, 2019

(51) Int. Cl.
*A24F 47/00* (2020.01)
*G06F 21/32* (2013.01)
*G06Q 20/40* (2012.01)
*G16H 10/60* (2018.01)

(52) U.S. Cl.
CPC ............ *A24F 47/002* (2013.01); *G06F 21/32* (2013.01); *G06Q 20/40145* (2013.01); *G16H 10/60* (2018.01)

(58) Field of Classification Search
CPC .. A24F 40/65; A24F 1/32; A24F 40/40; A24F 47/008; A24F 40/10; A24F 47/002; G07C 9/27; G07C 9/29; G06F 21/32; G06Q 20/40145; G16H 10/60
See application file for complete search history.

(56) References Cited

U.S. PATENT DOCUMENTS 10,531,693 B1 * 1/2020 Greenbaum ............ A24F 40/65
2014/0060552 A1 * 3/2014 Cohen .................... A24F 47/002
131/273
2014/0246035 A1 * 9/2014 Minskoff ............... A24F 47/008
131/329
2014/0322682 A1   10/2014 Baym et al.
(Continued)

FOREIGN PATENT DOCUMENTS

CN      103948177 A      7/2014
CN      104010539 A      8/2014
(Continued)

OTHER PUBLICATIONS

International search report dated May 7, 2020 in the corresponding international application No. PCT/CN2019/130317.

*Primary Examiner* — Brian E Miller
(74) *Attorney, Agent, or Firm* — Kilpatrick Townsend & Stockton LLP

(57) ABSTRACT

Electronic consumable devices (ECDs) are provided with integrated bio-traceability to facilitate user-based usage restriction, tracking, etc. For example, an individual legally purchases an ECD (e.g., an e-cigarette) from a vendor, and the ECD has a biosensor (e.g., fingerprint scanner) integrated therein. During the purchasing, the vendor uses a controller device to set up registration of the ECD for the individual, and the ECD cannot be used prior to registration. As part of the registration, the individual uses the biosensor to register a biometric signature, and the vendor's controller device confirms registration of the ECD. According to some embodiments, subsequent to registration, the ECD can be used only in connection with maintaining both device-level authorization based on communications with one or more remote controller devices and user-level authorization based on acquisition of the registered biometric signature by the integrated biosensor.

19 Claims, 6 Drawing Sheets

(56) References Cited

U.S. PATENT DOCUMENTS

| | | | | |
|---|---|---|---|---|
| 2015/0164144 A1* | 6/2015 | Liu | ................ | G06F 21/32 |
| | | | | 131/329 |
| 2015/0181945 A1* | 7/2015 | Tremblay | .............. | A24F 47/008 |
| | | | | 131/328 |
| 2015/0304401 A1* | 10/2015 | Liu | ................ | A24F 47/008 |
| | | | | 709/217 |
| 2017/0135407 A1* | 5/2017 | Cameron | .............. | A24F 47/008 |
| 2017/0196270 A1* | 7/2017 | Vick | ................ | G06F 21/32 |
| 2017/0308889 A1* | 10/2017 | Cameron | .............. | G07F 17/18 |
| 2018/0020720 A1* | 1/2018 | Matischek | .............. | G06F 21/34 |
| | | | | 131/329 |
| 2018/0043114 A1* | 2/2018 | Bowen | .............. | A61M 15/003 |
| 2018/0050171 A1* | 2/2018 | Tabert | ................ | A61B 5/7415 |
| 2018/0132530 A1* | 5/2018 | Rogers | ................ | H05B 1/0244 |
| 2018/0192702 A1* | 7/2018 | Li | ................ | A24F 47/008 |
| 2018/0263283 A1* | 9/2018 | Popplewell | .......... | A24B 15/167 |
| 2018/0296777 A1* | 10/2018 | Terry | ................ | A61M 11/042 |
| 2019/0014824 A1* | 1/2019 | Yazbeck | .............. | A61M 15/008 |
| 2019/0158938 A1* | 5/2019 | Bowen | ................ | A24F 47/008 |
| 2019/0197225 A1* | 6/2019 | Khalifa | ................ | G06K 9/22 |
| 2019/0272359 A1* | 9/2019 | Popplewell | .............. | G06F 21/32 |
| 2019/0307177 A1* | 10/2019 | Maeder | ................ | G01N 27/416 |
| 2020/0029619 A1* | 1/2020 | Sundberg | .............. | A24F 47/008 |
| 2020/0085105 A1* | 3/2020 | Barbaric | ................ | A24F 47/008 |
| 2020/0093180 A1* | 3/2020 | Qiu | ................ | H04W 4/023 |
| 2020/0110148 A1* | 4/2020 | Estripeau | .............. | H04W 4/029 |

FOREIGN PATENT DOCUMENTS

| | | |
|---|---|---|
| CN | 105451115 A | 3/2016 |
| CN | 108140120 A | 6/2018 |
| CN | 108451032 A | 8/2018 |
| CN | 108875340 A | 11/2018 |
| CN | 109581937 A | 4/2019 |
| CN | 109782670 A | 5/2019 |
| CN | 109983437 A | 7/2019 |
| WO | 2019000421 A1 | 1/2019 |

* cited by examiner

BIO-TRACEABLE ELECTRONIC CONSUMABLE DEVICE

TECHNICAL FIELD

This disclosure relates to consumable devices, and, more particularly, to bio-tracing of consumable devices, such as electronic cigarettes, for usage restriction, usage tracking, and other purposes.

BACKGROUND

Many consumable substances are becoming increasing available for consumption using various types of electronic consumable devices (ECDs). For example, tobacco, cannabis, and other plants can be processed into oils and/or other substances that are consumable using ECDs, such as electronic cigarettes ("e-cigarettes"), vaping devices, and the like. Similarly, ECDs can be used for electronic (e.g., automated) dispensing of medicine, or the like. In these and other cases, the consumable substances can have a strong impact on health, such that it can be desirable to ensure that only certain individuals are able to use such ECDs.

In many countries, there are restrictions relating to the sale of certain ECDs. For example, it may be illegal to sell e-cigarettes to individuals under a certain minimum age (e.g., 18 years old). Still, it can be relatively simple for a minor to obtain a ECD (e.g., by taking an ECD from an older sibling, parent, or other). Further, one the minor has obtained the ECD, the minor can often freely the ECD with friends. Along with increased availability of such ECDs, it has also become increasingly difficult to detect usage of such ECDs by minors and/or other unauthorized individuals. For example, many e-cigarettes and vaping devices are implemented in form factors that is hard for teachers, parents, and others to see, such as in packaging that looks like a USB thumb drive, or other small, ubiquitous electronic device. Moreover, even if a parent or teacher suspects unauthorized usage of such ECDs, they may have little recourse, other than to find and confiscate the ECD.

SUMMARY

Embodiments integrate bio-traceability into electronic consumable devices (ECDs) to facilitate user-based usage restriction, tracking, etc. For example, an individual legally purchases an ECD (e.g., an e-cigarette) from a vendor, and the ECD has a biosensor (e.g., fingerprint scanner) integrated therein. During the purchasing, the vendor uses a controller device to set up registration of the ECD for the individual, and the ECD cannot be used prior to registration. As part of the registration, the individual uses the biosensor to register a biometric signature, and the vendor's controller device confirms registration of the ECD. According to some embodiments, subsequent to registration, the ECD can be used only in connection with maintaining both device-level authorization based on communications with one or more remote controller devices and user-level authorization based on acquisition of the registered biometric signature by the integrated biosensor. Such device-level authorization can provide certain features, such as facilitating remote tracking of all registered devices, facilitating remote authorization and/or restriction of one or more devices (e.g., centrally disabling such devices in a particular vicinity), etc. Such user-level authorization can provide additional features, such as facilitating restricting of usage of the ECD only to authorized (registered) users, facilitating tracking of unauthorized usage attempts, facilitating tracking of usage (e.g., times, durations, frequency, etc.) by authorized users, etc.

According to one set of embodiments, an electronic consumable device is provided. The device includes: a consumable delivery module configured to contain a consumable substance and to selectively operate in one of a first mode or a second mode, the consumable delivery module configured to permit consumption of the consumable substance when operating in the first mode, and the consumable delivery module configured to restrict consumption of the consumable substance when operating in the second mode; a network module configured to communicate with a remote controller device via a wireless communication network, the network module associated with a network identifier; an interface module comprising a biosensor to obtain a biometric signature from a user; and a central processor, coupled with the consumable delivery module, the network module, and the interface module, to: direct, responsive to detecting a user interaction via the interface module, the network module to communicate an authorization transaction with the remote controller device via the wireless communication network; determine whether to authorize the electronic consumable device in accordance with the authorization transaction; and in response to determining to authorize the electronic consumable device: direct the interface module to activate the biosensor for acquisition of the biometric signature from the user; process the biometric signature to determine whether to authorize the user; and direct the consumable delivery module to operate in the first mode in accordance with determining to authorize the user.

According to another set of embodiments, a method is provided for bio-tracing an electronic consumable device. The method includes: detecting a user interaction with the electronic consumable device; communicating, responsive to the detecting, an authorization transaction with a remote controller device via a wireless communication network; determining whether to authorize the electronic consumable device in accordance with the authorization transaction; and in response to determining to authorize the electronic consumable device: activating a biosensor of the electronic consumable device to acquire a biometric signature from the user; processing the biometric signature to determine whether to authorize the user; and directing a consumable delivery module of the electronic consumable device to operate in a first mode in response to determining to authorize the user, the consumable delivery module configured to contain a consumable substance and to selectively operate in one of the first mode or a second mode, the consumable delivery module configured to permit consumption of the consumable substance when operating in the first mode, and the consumable delivery module configured to restrict consumption of the consumable substance when operating in the second mode.

According to another set of embodiments, an electronic consumable device is provided. The device includes: a central processor; and a memory having instructions stored thereon, which, when executed, cause the processor to: detect a user interaction with the electronic consumable device; communicate, responsive to the detecting, an authorization transaction with a remote controller device via a wireless communication network; determine whether to authorize the electronic consumable device in accordance with the authorization transaction; and in response to determining to authorize the electronic consumable device: activate a biosensor of the electronic consumable device to acquire a biometric signature from the user; process the biometric signature to determine whether to authorize the user; and direct a consumable delivery module of the electronic consumable device to operate in a first mode in response to determining to authorize the user, the consumable delivery module configured to contain a consumable substance and to selectively operate in one of the first mode or a second mode, the consumable delivery module configured to permit consumption of the consumable substance when operating in the first mode, and the consumable delivery module configured to restrict consumption of the consumable substance when operating in the second mode.

BRIEF DESCRIPTION OF THE DRAWINGS

The accompanying drawings, referred to herein and constituting a part hereof, illustrate embodiments of the disclosure. The drawings together with the description serve to explain the principles of the invention.

Figure 1:
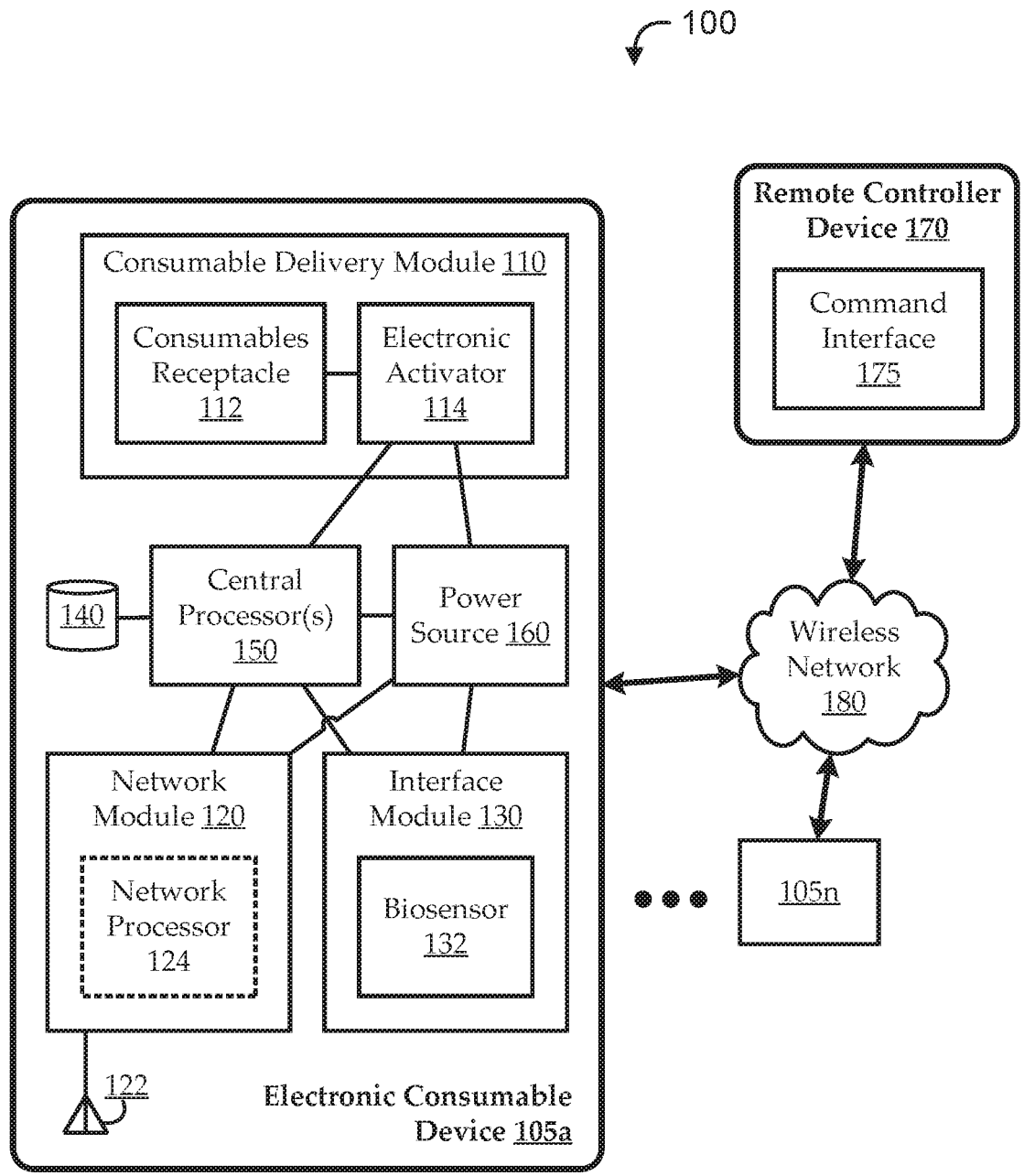
FIG. 1 shows a communication environment in which an illustrative remote controller device is in communication with one or more electronic consumption devices (ECDs) over one or more wireless networks, according to various embodiments.

In the appended figures, similar components and/or features can have the same reference label. Further, various components of the same type can be distinguished by following the reference label by a second label that distinguishes among the similar components. If only the first reference label is used in the specification, the description is applicable to any one of the similar components having the same first reference label irrespective of the second reference label.

DETAILED DESCRIPTION

Many consumable substances are becoming increasing available for consumption using various types of electronic consumable devices (ECDs). For example, tobacco, cannabis, and other plants can be processed into oils and/or other substances that are consumable using ECDs, such as electronic cigarettes ("e-cigarettes"), vaping devices, and the like. Similarly, ECDs can be used for electronic (e.g., automated) dispensing of medicine, or the like. In these and other cases, the consumable substances can have a strong impact on health, such that it can be desirable to ensure that only certain individuals are able to use such ECDs.

In many countries, there are restrictions relating to the sale of certain ECDs. For example, it may be illegal to sell e-cigarettes to individuals under a certain minimum age (e.g., 18 years old). Still, it can be relatively simple for a minor to obtain a ECD (e.g., by taking an ECD from an older sibling, parent, or other). Further, one the minor has obtained the ECD, the minor can often freely the ECD with friends. Along with increased availability of such ECDs, it has also become increasingly difficult to detect usage of such ECDs by minors and/or other unauthorized individuals. For example, many e-cigarettes and vaping devices are implemented in form factors that is hard for teachers, parents, and others to see, such as in packaging that looks like a USB thumb drive, or other small, ubiquitous electronic device. Moreover, even if a parent or teacher suspects unauthorized usage of such ECDs, they may have little recourse, other than to find and confiscate the ECD.

Embodiments described herein integrate bio-traceability into ECDs to facilitate user-based usage restriction, tracking, etc. For example, an individual legally purchases an e-cigarette from a vendor, and the e-cigarette has a fingerprint scanner integrated therein. During the purchasing, the vendor uses a controller device to set up registration of the e-cigarette for the individual, and the e-cigarette cannot be used prior to registration. As part of the registration, the individual uses the fingerprint scanner to register a fingerprint, and the vendor's controller device confirms registration of the e-cigarette (e.g., a unique identifier) with the registered fingerprint. Subsequently, the e-cigarette can be used by the individual, but only in connection with providing the registered fingerprint. Associating the registered fingerprint with usage can provide various features. For example, such an association can facilitate restricting of usage of the e-cigarette only to authorized (registered) users, can facilitate tracking of unauthorized usage attempts, can facilitate tracking of usage (e.g., times, durations, frequency, etc.) by authorized users, etc. Further, association of the controller device with the e-cigarette can provide additional features. For example, such an association can facilitate remote tracking of all registered devices, can facilitate remote authorization and/or restriction of one or more devices (e.g., centrally disabling such devices in a particular vicinity), etc.

These and other features of various embodiments are described herein. In the following description, numerous specific details are provided for a thorough understanding of the present invention. However, it should be appreciated by those of skill in the art that the present invention may be realized without one or more of these details. In other examples, features and techniques known in the art will not be described for purposes of brevity.

FIG. 1 shows a communication environment 100 in which an illustrative remote controller device 170 is in communication with one or more electronic consumption devices (ECDs) 105 over one or more wireless networks 180, according to various embodiments. As described herein, embodiments can operate in context of types of consumable materials for which user-based restriction and/or tracking is desirable, and embodiments can facilitate such user-based restriction and/or tracking using bio-tracing. Bio-tracing can involve registering one or more bio-signatures (e.g., fingerprint patterns, voice patterns, etc.) with the ECD 105 to indicate one or more authorized users of the ECD 105. Registering the ECD 105 can also involve associating one or more remote controller devices 170 with the ECD 105 (e.g., using a command interface 175 of the remote controller device 170). In some embodiments, the ECD 105 is unusable unless both the ECD 105 is authorized for use by the remote controller device(s) 170 and the user attempting access to the ECD 105 is authorized by the user's registered bio-signature. To enable such functionality, the ECD 105 can include some or all of a consumable delivery module 110, a network module 120, an interface module 130, and memory 140.

Some or all of the components of the ECD 105 can be powered by a power source 160. The power source 160 can include any suitable one or more power sources 160, such as one or more receptacles for receiving one or more batteries; one or more integrated rechargeable batteries, capacitors, or other charge storage devices; one or more interfaces to connect the ECD 105 to line power (e.g., a port to couple the ECD 105 with a wall outlet); etc. Embodiments of the ECD 105 include a central processor 150 to direct operation of some or all of the other components of the ECD 105. The central processor 150 can include any suitable number and type of processor.

Embodiments of the consumable delivery module 110 include a consumables receptacle 112 to contain a consumable substance, such as plant material (e.g., tobacco), consumable plant oil (e.g., tobacco oil, cannabis oil), medication (e.g., pills, caplets, etc.), or the like. The consumable delivery module 110 can selectively operate in multiple modes, such as in one of a first mode or a second mode. When the consumable delivery module 110 is operating in the first mode (e.g., operational mode, unrestricted mode, unlocked mode, etc.), the consumable delivery module 110 permits consumption of the consumable substance. When the consumable delivery module 110 is operating in the second mode (e.g., non-operational mode, restricted mode, locked mode, etc.), the consumable delivery module 110 restricts consumption of the consumable substance. Some embodiments of the ECD 105 include an electronic activator 114, and permitting or restricting consumption involves activating or de-activating the electronic activator 114.

Permitting or restricting consumption can be implemented differently for different types of ECDs 105 and/or for different types of consumable substances. Some embodiments of ECDs 105 are implemented as e-cigarettes or vaping devices. In such embodiments, the consumables receptacle 112 includes a chamber to hold a quantity of consumable plant oil, a receptacle to hold an insertable container of consumable plant oil, or any other suitable receptacle. In some such embodiments, the electronic activator 114 includes an electronic vaporizer (e.g., a heater, ultrasonic vaporizer, etc.), and related components, to convert the consumable plant oil into a consumable vapor. In some such embodiments, permitting consumption of the consumable material (e.g., by operating the ECD 105 in the first mode) involves activating the electronic vaporizer, for example, by turning on the electronic vaporizer, establishing a connection (e.g., completing a circuit using an electronic switch) between the electronic vaporizer and the power supply 160, etc.; restricting consumption of the consumable material (e.g., by operating the ECD 105 in the second mode) involves de-activating the electronic vaporizer, for example, by turning off the electronic vaporizer, disconnecting the electronic vaporizer from the power supply 160, etc. Other embodiments of ECDs 105 are implemented as electronic medicine dispensing devices. In such embodiments, the consumables receptacle 112 includes a chamber to hold a quantity of medicine (e.g., pills, liquid, etc.). In some such embodiments, the electronic activator 114 includes an electronic lock on the receptacle. In some such embodiments, permitting consumption of the consumable material (e.g., by operating the ECD 105 in the first mode) involves setting the electronic lock in an unlocked state to permit access by a user to the medicine in the consumables receptacle 112; restricting consumption of the consumable material (e.g., by operating the ECD 105 in the second mode) involves setting the electronic lock in a locked state to prevent access by a user to the medicine in the consumables receptacle 112.

In some embodiments, restricting consumption involves preventing consumption. For example, in an e-cigarette implementation of an ECD 105, consumption can be prevented by disconnecting the electronic vaporizer from the power source; in a medicine dispenser implementation of an ECD 105, consumption can be prevented by securely electronically locking the medicine receptacle. In other embodiments, restricting consumption involves limiting or frustrating consumption. For example, in an e-cigarette implementation of an ECD 105, consumption can be frustrated by requiring additional user interaction for the electronic activator 114 to operate in the first mode (e.g., requiring a user to hold down a button during use, etc.), by activating an indicator (e.g., illuminating a red LED, playing a sound, etc.) during use, by limiting the amount of consumable substance that is consumed per use, etc.; in a medicine dispenser implementation of an ECD 105, consumption can be frustrated by electronically locking the medicine receptacle in a manner that can be opened with additional effort and/or other additional interaction, etc.

Embodiments of the network module 120 include a wireless antenna 122 coupled with a network processor 124 (e.g., implemented as part of, or as separate from, the central processor 150). The network module 120 can facilitate communications between the ECD 105 and one or more remote controller devices 170 via the wireless communication network(s) 180. The network module 120 can include any suitable components for enabling communications via any suitable type of wireless communication network(s) 180 (and/or wired communications networks), such as physical and/or logical ports, protocols, circuits, etc. For example, the wireless communication network(s) 180 can include Bluetooth networks, ZigBee networks, wireless fidelity (WiFi) networks, near-field communications (NFC) networks, radiofrequency identifier (RFID) networks, wireless local area networks (Wi-LANs), narrow-band Internet of Things (nb-IoT) networks, cellular networks, satellite networks, etc.

Embodiments of the ECD 105 are associated with an identifier (e.g., a unique identifier). In some implementations, the identifier is a network identifier, which enables identification of the ECD 105 by the remote controller device(s) 170 via the wireless communication network(s) 180. For example, the wireless identifier can be hardcoded in the central processor 150, stored in the memory 140, and/or otherwise accessible for wireless identification of the ECD 105. As described herein, facilitating identification of the ECD 105 by the remote controller device(s) 170 can contribute to various functions, such as registration of the ECD 105 by a remote controller device 170, tracking of usage of the ECD 105 by one or more remote controller devices 170, remote control of the ECD 105 by one or more remote controller devices 170, etc.

Embodiments of the interface module 130 include one or more biosensors 132 to obtain a biometric signature from a user. The one or more biosensors 132 can include any suitable type of sensor for acquiring a biometric signature from an individual user. The biometric signature can be compared against biometric data stored in the memory 140 and/or accessible via the wireless communication network(s) 180 (e.g., stored by one or more remote controller devices 170). Biometric data, including biometric signatures, can be stored in any suitable manner for enabling the bio-tracing operations described herein. For the sake of expediency, portions of the description and claims refer to the biometric signature, or the like, both as what is obtained by the one or more biosensors 132 and as what is stored during registration. In some implementations, the stored biometric data and the obtained biometric signature are substantially identical. Typically, however, the stored biometric data includes different (e.g., more) information that whatever biometric signature is acquired at any particular time by the one or more biosensors 132. For example, during registration, an individual may use the one or more biosensors 132 (or a different one or more biosensors 132, such as integrated with, or coupled with a remote controller device 170) to generate a biometric profile for storage. Registering a larger amount of biometric data can facilitate performance of bio-tracing functions based on acquisition of smaller amounts of valid biometric signature data at any particular time.

For example, the one or more biosensors 132 can include a fingerprint sensor to acquire a user's fingerprint pattern. During registration, fingerprint data can be acquired multiple times to generate a more complete profile of the fingerprint pattern, such that subsequent acquisition of partial fingerprints, partially obscured fingerprints, etc. can still be used for bio-tracing functions. The fingerprint sensor can be implemented in any suitable manner. In some implementations, the fingerprint sensor is an optical fingerprint sensor that uses mono-spectral acquisition, multi-spectral acquisition, etc. Other embodiments of the one or more biosensors 132 can include any other suitable biosensors, such as a biomedical sensor to detect one or more biological properties of a user, such as a property of a user's blood, heartbeat, etc.; a microphone to detect a voice signature and/or passphrase of a user; etc. In some implementations, the one or more biosensors 132 are implemented as low-power sensors that remain always on, so as to remain in a state ready for acquisition. In other implementations, the one or more biosensors 132 switch to a low-power (e.g., standby power) mode, or switch off completely, when not in use. In such implementations, one or more other elements of the interface module 130 (e.g., a switch, button, gyroscopic sensor, etc.) can trigger activation of the one or more biosensors 132.

In some embodiments, the ECD 105 cannot be used until the ECD 105 has been registered. As described herein, such registration can involve registration of the ECD 105 with one or more remote controller devices 170 (e.g., in accordance with an associated network identifier) and registration of the ECD 105 with one or more authorized users (e.g., in accordance with associated one or more biometric signatures). Some illustrative embodiments of such registration are shown in FIGS. 2A and 2B.

Figure 2A:
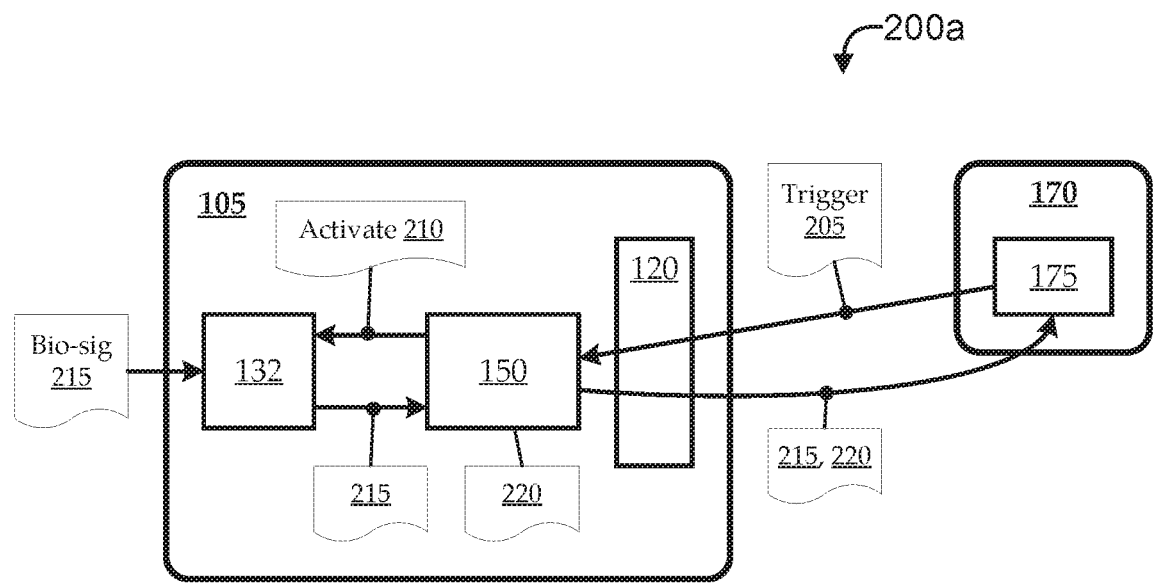
FIG. 2A shows a block diagram of a first illustrative registration procedure, according to various embodiments.
Figure 2B:
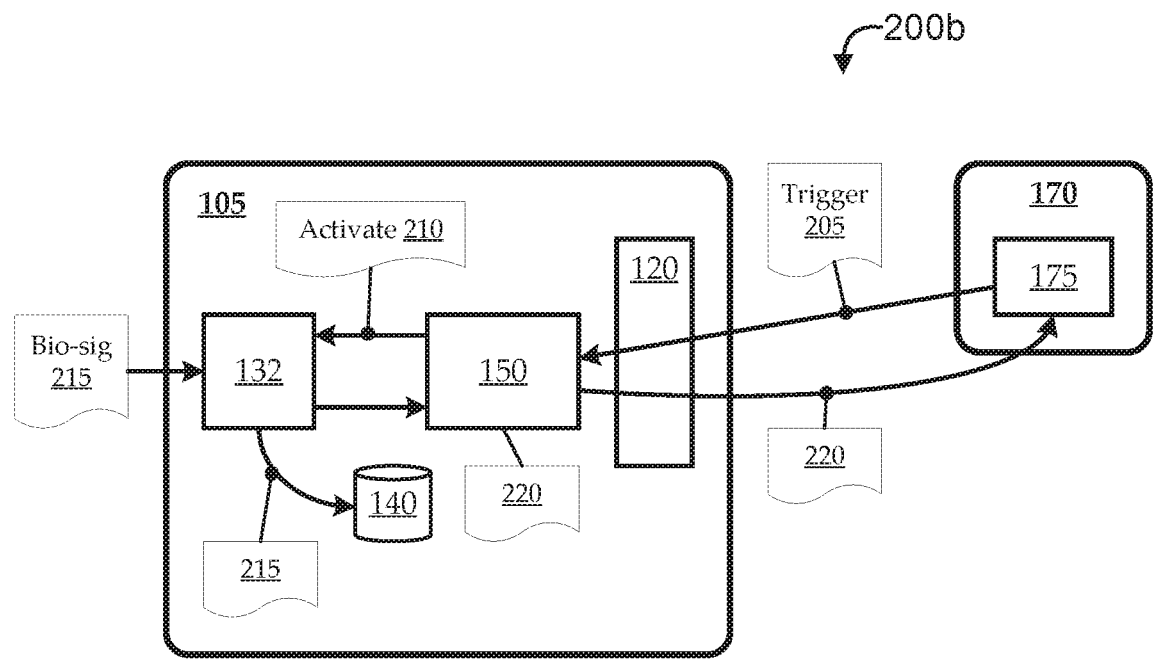
FIG. 2B shows a block diagram of a second illustrative registration procedure, according to various embodiments.

FIG. 2A shows a block diagram of a first illustrative registration procedure 200a, according to various embodiments. The registration procedure 200a can begin by the ECD 105 receiving a registration trigger signal 205 from a remote controller device 170 (e.g., issued via a command interface 175). In some embodiments, the registration trigger signal 205 is received by the central processor 150 of the ECD 105 via the network module 120 of the ECD 105. For example, when the ECD 105 is first purchased from a vendor, factory reset, etc., the ECD 105 can be in a state in which registration is permitted. While in that state, communications can be established between the ECD 105 and the remote controller device 170. For example, the communications can be established by wired connection (e.g., by plugging the ECD 105 into the remote controller device 170), by wireless communications (e.g., by wireless pairing), and/or in any other suitable manner. In one implementation, upon detecting the established communications link while in an unregistered state, the ECD 105 initiates the registration procedure 200a. In another implementation, upon detecting the established communications link with an unregistered ECD 105, the remote controller device 170 initiates the registration procedure 200a. In other implementations, the vendor or other authorized user can initiate the registration procedure 200a via the command interface 175.

Responsive to receiving the registration trigger signal 205, the central processor 150 can generate an activation signal 210 to direct the interface module 130 to activate the biosensor 132. With the biosensor 132 activated, the biosensor 132 can be used to acquire the biometric signature 215 from the user. As described above, such acquisition can involve acquiring more and/or different biometric information from the user from which the biometric signature 215 can be derived. The biometric signature 215 can be passed to the central processor 150. In some implementations, the central processor 150 continues to acquire biometric information until a sufficient amount of biometric information is received. For example, the command interface 175 can be configured to guide acquisition of the biometric information by indicating to the user which biometric information is missing, whether enough biometric information has successfully been acquired, etc.

Embodiments of the central processor 150 can then transmit registration response data to the remote controller device 170 (e.g., via the network module 120 and one or more wired and/or wireless networks). The registration response data can include the biometric signature 215 and a network identifier 220 associated with the central processor 150 and/or the ECD 105 generally. Alternatively, the network identifier 220 can be generated by the command interface 175 and assigned to and/or transmitted to the ECD 105 during the registration procedure 200a (e.g., as part of the registration trigger signal 205, or otherwise). In some embodiments, when the remote controller device 170 receives the biometric signature 215 and the network identifier 220, the remote controller device 170 can commence with registration. In some implementations, the remote controller device 170 stores the biometric signature 215 in association with the network identifier 220, thereby registering the biometric signature 215 at the remote controller device 170 as an authorized user in association with the network identifier 220. In other implementations, the biometric signature 215 and/or other descriptive information about the user (e.g., entered into the command interface 175 by the vendor, the user, etc.) is audited to verify whether the user is permitted to become an authorized user. For example, the vendor can check the user's identification, prescription, or the like, and/or otherwise verify the user.

FIG. 2B shows a block diagram of a second illustrative registration procedure 200b, according to various embodiments. The registration procedure 200b is similar to the first registration procedure 200a, except that the biometric registration is handled locally by the ECD 105. For example, similar to the first registration procedure 200a, the second registration procedure 200b can begin by the ECD 105 receiving a registration trigger signal 205 from a remote controller device 170. Responsive to receiving the registration trigger signal 205, the central processor 150 can generate an activation signal 210 to direct the interface module 130 to activate the biosensor 132. With the biosensor 132 activated, the biosensor 132 can be used to acquire the biometric signature 215 from the user.

The biometric signature 215 can be stored in memory 140 local to the ECD 105. As described above, the stored information can include additional and/or different biometric information. In such embodiments, the biometric signature 215 and/or other information may or may not be passed to the central processor 150. In some implementations, the central processor 150 and/or the command interface 175 of the remote controller device 170 can assist with acquiring sufficient biometric information for storage in the memory 140. In some implementations, information is passed to, and/or generated by, the central processor 150 indicating that sufficient biometric signature 215 data has been acquired and stored. Embodiments of the central processor 150 can then transmit registration response data to the remote controller device 170 (e.g., via the network module 120 and one or more wired and/or wireless networks).

In some embodiments of the second registration procedure 200b, the registration response data can include only the network identifier 220, and/or other information indicating successful biometric registration. In such embodiments, the when the remote controller device 170 receives the network identifier 220, the remote controller device 170 can commence with registration without the biometric signature 215. In other implementations, though not shown, some or all of the acquired biometric information can be stored in the local memory 140 of the ECD 105 and also transmitted to the remote controller device 170. In other embodiments, some or all of the biometric information can be stored in one or more other locations, such as in a remote server accessible via one or more networks. As in the first registration procedure 200a, embodiments can include further user verifications, such as by verifying the user's identification, age, prescriptions, etc.

Figure 3:
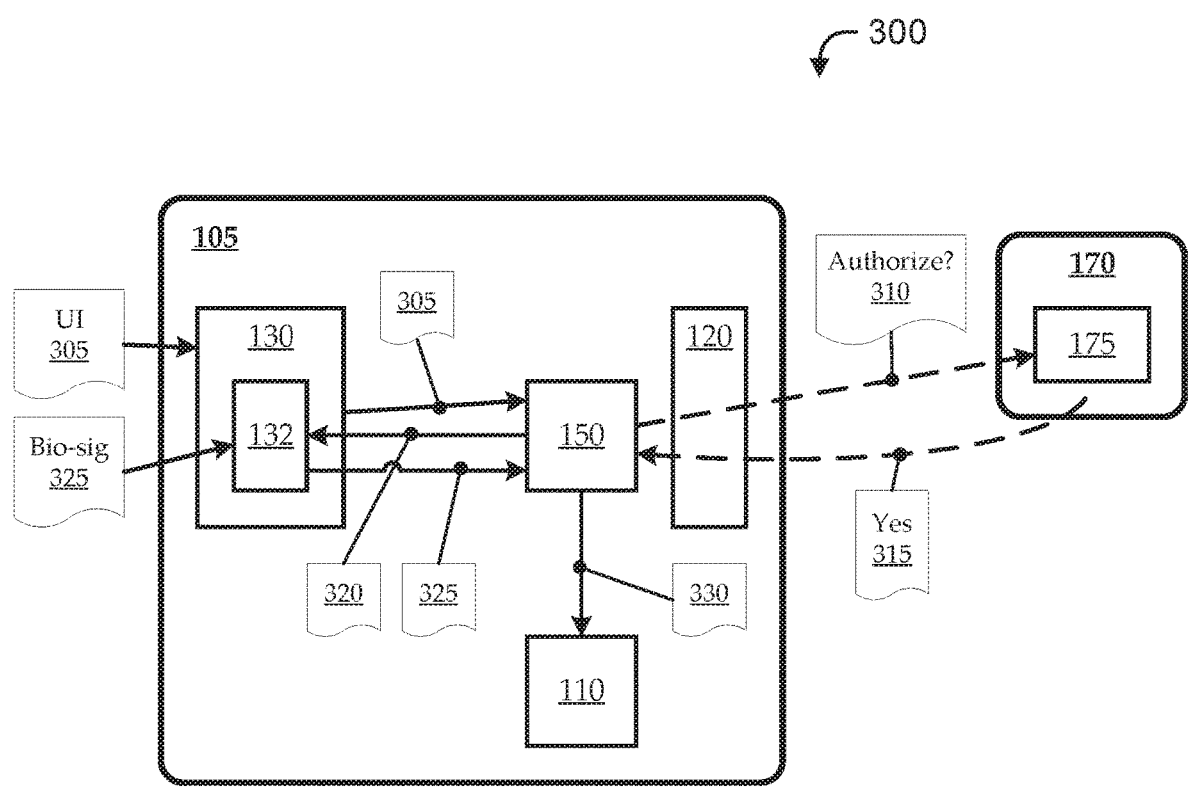
FIG. 3 shows a block diagram of a usage procedure by which the ECD is successfully used by a registered user of the ECD, according to various embodiments.

Subsequent to registration, the ECD 105 can be used to consume a consumable material. FIG. 3 shows a block diagram of a usage procedure 300 by which the ECD 105 is successfully used by a registered user of the ECD 105, according to various embodiments. The usage procedure 300 can begin upon detection of a user interaction 305 with the interface module 130 of the ECD 105. In some implementations, the interface module 130 includes one or more dedicated controls, and detecting the user interaction 305 involves detecting an interaction with one of the dedicated controls. For example, when a user presses a particular button on the ECD 105, the usage procedure 300 commences. In other implementations, the interface module 130 includes one or more "always-on" sensors (i.e., sensors that remain ready to detect interaction, even while the biosensor 132 is deactivated), and detecting the user interaction 305 involves detecting an interaction with one of the always-on sensors. For example, when a user picks up the ECD 105, an always-on gyroscopic sensor, or the like, automatically detects the interaction, and the usage procedure 300 commences. In other implementations, one or more biosensors 132 can be used to detect the user interaction 305. For example, a fingerprint sensor can be implemented to operate in a low-power mode, in which it is capable of detecting interaction (e.g., by detecting optical interference with a photodetector in the optical system of the fingerprint sensor), but is not capable of acquiring (or processing) a biometric signature 215. As such, the fingerprint sensor can be de-activated for use as the biosensor 132, while still being active for use in detecting the user interaction 305 to commence the usage procedure 300.

The user interaction 305 (or a trigger signal generated in response to the user interaction 305, can be passed to the central processor 150. In response to detecting the user interaction 305, the central processor 150 can direct the network module 120 to communicate an authorization transaction with the remote controller device 170 (e.g., via the wireless communication network 180). In some embodiments, communicating the authorization transaction involves the ECD 105 communicating an authorization request 310 to the remote controller device 170, and receiving an authorization response from the remote controller device 170 in response to the authorization request 310. In the illustrated successful usage procedure 300, the authorization response is a positive authorization response 315. In other embodiments, communicating the authorization transaction involves the ECD 105 communicating an authorization request 310 to the remote controller device 170 (e.g., pinging the remote controller device 170), and waiting for a response. In some such embodiments, any response from the remote controller device 170 can indicate successful authorization, such that any response is a positive authorization response 315. For example, after transmitting the authorization request 310 to the remote controller device 170, the ECD 105 can wait for a predetermined period of time, after which authorization is automatically assumed to be denied, if no response has been received. In other such embodiments, any response from the remote controller device 170 can indicate unsuccessful authorization, such that any response is a negative authorization response. For example, after transmitting the authorization request 310 to the remote controller device 170, the ECD 105 can wait for a predetermined period of time, after which authorization is automatically assumed to be granted, if no response has been received.

In response to receiving an indication of a successful device authorization, the central processor 150 can generate and transmit an activation trigger signal 320 to direct the interface module 130 to activate the biosensor 132 (or multiple biosensors 132) for acquisition of biometric data from the user. With the biosensor 132 active, the user can interact with the biosensor 132, and the biosensor 132 can acquire the biometric signature 325 from the user. The acquired biometric signature 325 can be passed to the central processor 150 for user authorization. In some embodiments, such authorization is performed locally by comparing the acquired biometric signature 325 with locally stored biometric information. In other embodiments, such authorization involved communicating the acquired biometric signature 325 to the remote controller device 170, and the remote controller device 170 compares the acquired biometric signature 325 with biometric information stored at the remote controller device 170, at a remote server, and/or in any other suitable location. Some implementations can balance convenience of use by an authorized user against restricting of use by unauthorized users. For example, overly strong biometric authorization can tend to cause an abundance of false negatives, which can lead to frustration when an authorized user is regularly denied access; while overly weak biometric authorization can tend to cause an abundance of false positives, which may tend to permit unauthorized usage of the ECD 105.

In general, embodiments maintain the one or more biosensors 132 in an inactive state until the ECD 105 is authorized at the device level in accordance with the authorization transaction with the remote controller device 170. In such embodiments, only after successful device-level authorization are the biosensors 132 available for acquisition of biometric data. Even at that point, however, the consumable materials in the ECD 105 still cannot be consumed without user-level authorization. Such user-level authorization involves using the biosensors 132 to acquire the biometric signature 325 of the user, and successfully matching the acquired biometric signature 325. to biometric information of an authorized user. Having successfully performed both device-level authorization and user-level authorization, the central processor 150 can configure the consumable delivery module 110 for consumption. Embodiments of the central processor 150 can generate and transmit a mode select signal 330 to the consumable delivery module 110. As described above, the mode select signal 330 can direct the consumable delivery module 110 to operate in a mode (e.g., the first mode, as described above) in which the electronic activator 114 is configured to permit consumption of consumable materials in the consumables receptacle 112.

Figure 4A:
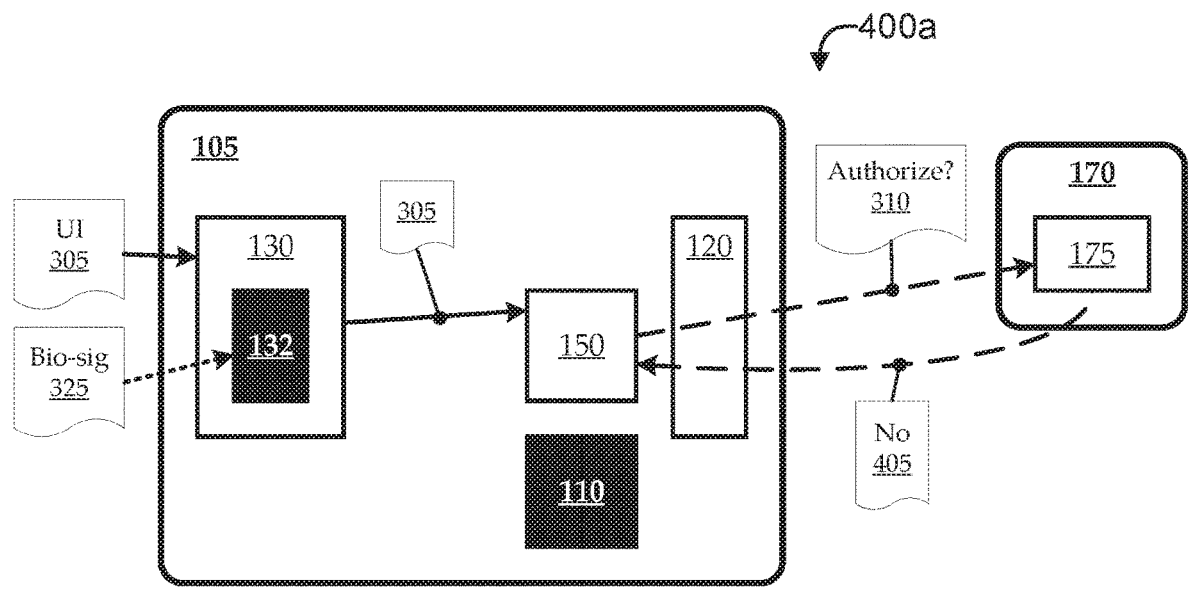
FIGS. 4A and 4B show block diagrams of illustrative unsuccessful usage procedures, according to various embodiments.
Figure 4B:
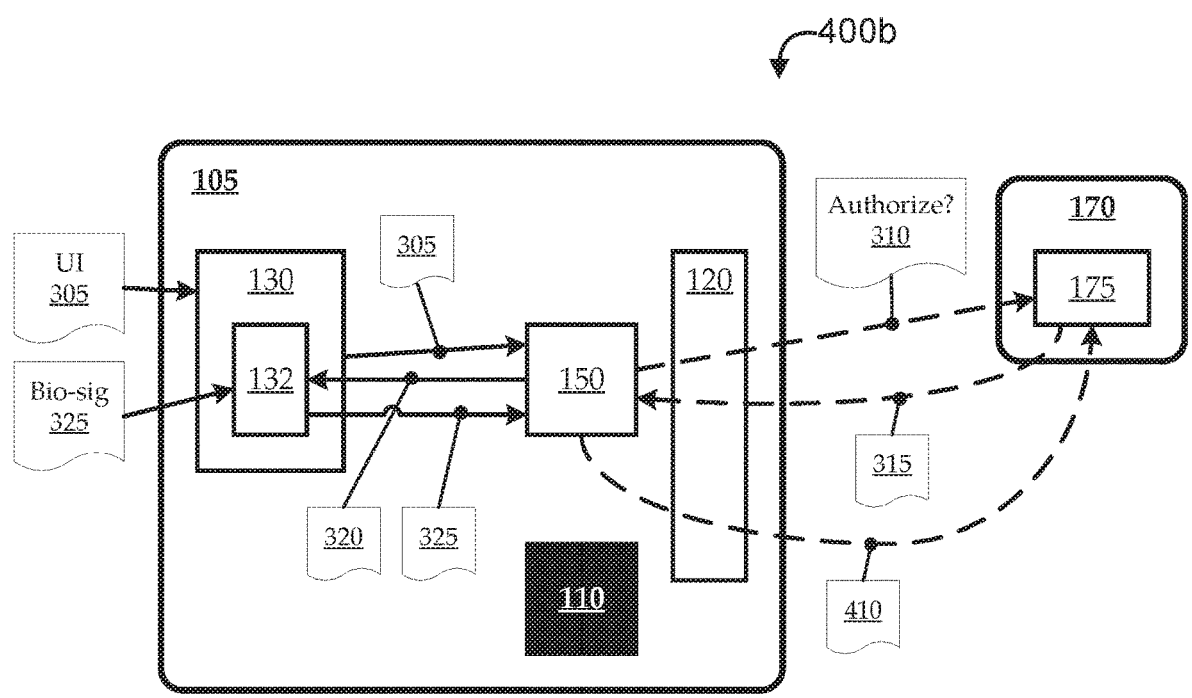

FIGS. 4A and 4B show block diagrams of illustrative unsuccessful usage procedures 400, according to various embodiments. In particular, FIG. 4A shows an illustrative unsuccessful usage procedures 400a in which device-level authorization is unsuccessful. FIG. 4B shows an illustrative unsuccessful usage procedures 400b in which device-level authorization is successful, but user-level authorization is unsuccessful. Both unsuccessful usage procedures 400 can begin (as in FIG. 3) upon detection of a user interaction 305 with the interface module 130 of the ECD 105. The user interaction 305 (or a trigger signal generated in response to the user interaction 305, can be passed to the central processor 150. In response to detecting the user interaction 305, the central processor 150 can direct the network module 120 to communicate an authorization transaction with the remote controller device 170 (e.g., via the wireless communication network 180).

In the case illustrated by FIG. 4A, the authorization transaction results in an explicit or implicit negative authorization response 405 from the remote controller device 170. As described above, in some implementations, such communicating of the authorization transaction involves bi-directional communications (e.g., an authorization request 310 followed by an explicit negative authorization response 405). In other implementations, such communicating of the authorization transaction involves one-way communications from the ECD 105 (e.g., the ECD 105 pings the remote controller device 170, and a lack of any response indicates an implicit negative authorization response 405). In other implementations, such communicating of the authorization transaction involves one-way communications from the remote controller device 170 (e.g., the ECD 105 listens for communications from the remote controller device 170, and a lack of any response indicates an implicit negative authorization response 405; or the ECD 105 listens for communications from the remote controller device 170 and receives an explicit negative authorization response 405). Thus, in the case of FIG. 4A, the device-level authorization has failed. As such, the central processor 150 does not activate the biosensor(s) 132 and does not activate the consumable delivery module 110 to permit consumption. As illustrated, a user can attempt to provide a biometric signature 325 to the biosensor 132, but the biometric signature 325 will not be acquired (or will not be received and/or processed by the central processor 150).

In the case illustrated by FIG. 4B, the authorization transaction results in an explicit or implicit positive authorization response 315 from the remote controller device 170, as in FIG. 3. In response to receiving an indication of a successful device authorization, the central processor 150 can generate and transmit an activation trigger signal 320 to direct the interface module 130 to activate the biosensor 132 (or multiple biosensors 132) for acquisition of biometric data from the user. With the biosensor 132 active, the user can interact with the biosensor 132, and the biosensor 132 can acquire the biometric signature 325 from the user. The acquired biometric signature 325 can be passed to the central processor 150 for user authorization. The user-level authorization can be performed in any suitable manner, such as described with reference to FIG. 3. In the case of FIG. 4B, the user-level (biometric) authorization fails. Thus, the central processor 150 does not activate the consumable delivery module 110 to permit consumption.

Failure of the user-level authorization can trigger different actions in different embodiments. In some embodiments, the consumable delivery module 110 is maintained in an inactive (e.g., locked, disconnected, etc.) mode, except when there is successful device-level and user-level authorization; only then, the central processor 150 changes the mode of the consumable delivery module 110 to permit consumption. In other embodiments, the consumable delivery module 110 is maintained in an active (e.g., unlocked, connected, etc.) mode, except when there is unsuccessful device-level and user-level authorization; only then, the central processor 150 changes the mode of the consumable delivery module 110 to restrict consumption. In other embodiments, unsuccessful user-level authorization (or repeated unsuccessful user-level authorization) can trigger the central processor 150 to change the mode of the consumable delivery module 110 to further restrict consumption (e.g., the ECD 105 becomes completely unusable after a threshold number of unsuccessful access attempts have been detected).

In some embodiments, unsuccessful device-level and/or user-level authorization can be tracked by the ECD 105 and/or by a remote controller device 170. As illustrated in FIG. 4B, in some implementations, the ECD 105 can transmit an unauthorized event message 410 to the remote controller device 170 (while the message is illustrated only in context of FIG. 4B, such a message can also be sent in context of FIG. 4A, or any other suitable context). For example, in response to an unsuccessful user-level authorization, the remote controller device 170 can log the unsuccessful access attempt, along with any desired contextual information, such as time, location, network identifier, etc. In some cases, the acquired biometric signature 325 can be matched against a database of unauthorized users, and the identity of the attempting user can be logged in association with the unsuccessful access attempt.

The different types and levels of authorization can be used in different ways, according to different implementations. In some implementations, as illustrated by FIGS. 3, 4A, and 4B, device-level authorization and user-level authorization are performed in response to detecting a user interaction 305. In other implementations, device-level authorization is performed periodically. For example, the ECD 105 checks in with a particular remote controller device 170, or any remote controller devices 170 in the vicinity, according to a predetermined frequency (e.g., by sending a burst communication once per half-hour, once per ten minutes, etc.). In such implementations, the user-level authorization may still be implemented responsively, for example, responsive to a successful device-level authorization and resulting activation of the biosensor(s) 132. One or both levels of authorization can also be maintained for the same or different amounts of time. For example, in implementations in which device-level authorization is performed periodically, a resulting device-level authorization determination (e.g., whether the ECD 105 is authorized or not based on any given device-level authorization) can be considered valid until a next device-level authorization. Alternatively, a positive device-level authorization determination can be considered valid until some number of consecutive unsuccessful device-level authorization determinations are made, and/or a negative device-level authorization determination can be considered valid until some number of consecutive successful device-level authorization determinations are made.

With the ECD 105 in a device-level-authorized state, the user-level authorization can also be performed in various manners. In some implementations, use of the ECD 105 requires the user to maintain interaction with a biosensor 132 (e.g., keep a finger on the fingerprint sensor) during use, and user-level authorization involves repeatedly (e.g., continuously, periodically, etc.) acquiring, processing, and verifying the user's biometric signature 325. In other implementations, once a successful user-level authorization determination has been made, the determination can remain valid for a predetermined duration (e.g., for two hours). In other implementations, once a successful user-level authorization determination has been made, the determination can remain valid until a particular trigger event is detected. For example, the ECD 105 remains authorized (both at a device level and at a user level) until sensors detect that the ECD 105 has been put down, moved a certain threshold distance, moved out of range of a particular remote controller device 170, etc.

In these and other implementations, expiration of one or both levels of authorization can be handled in various ways. In some implementations in which device-level authorization and/or user-level authorization is valid for some duration of time, the ECD 105 can automatically revert to a state in which consumption is restricted upon expiration of that duration. For example, if user-level authorization is valid for two hours, the central processor 150 can maintain the consumable delivery module 110 in a consumption-permissive mode during those two hours, and the central processor 150 can automatically switch the consumable delivery module 110 to a consumption-restrictive mode at the end of the two hours.

Figure 5:
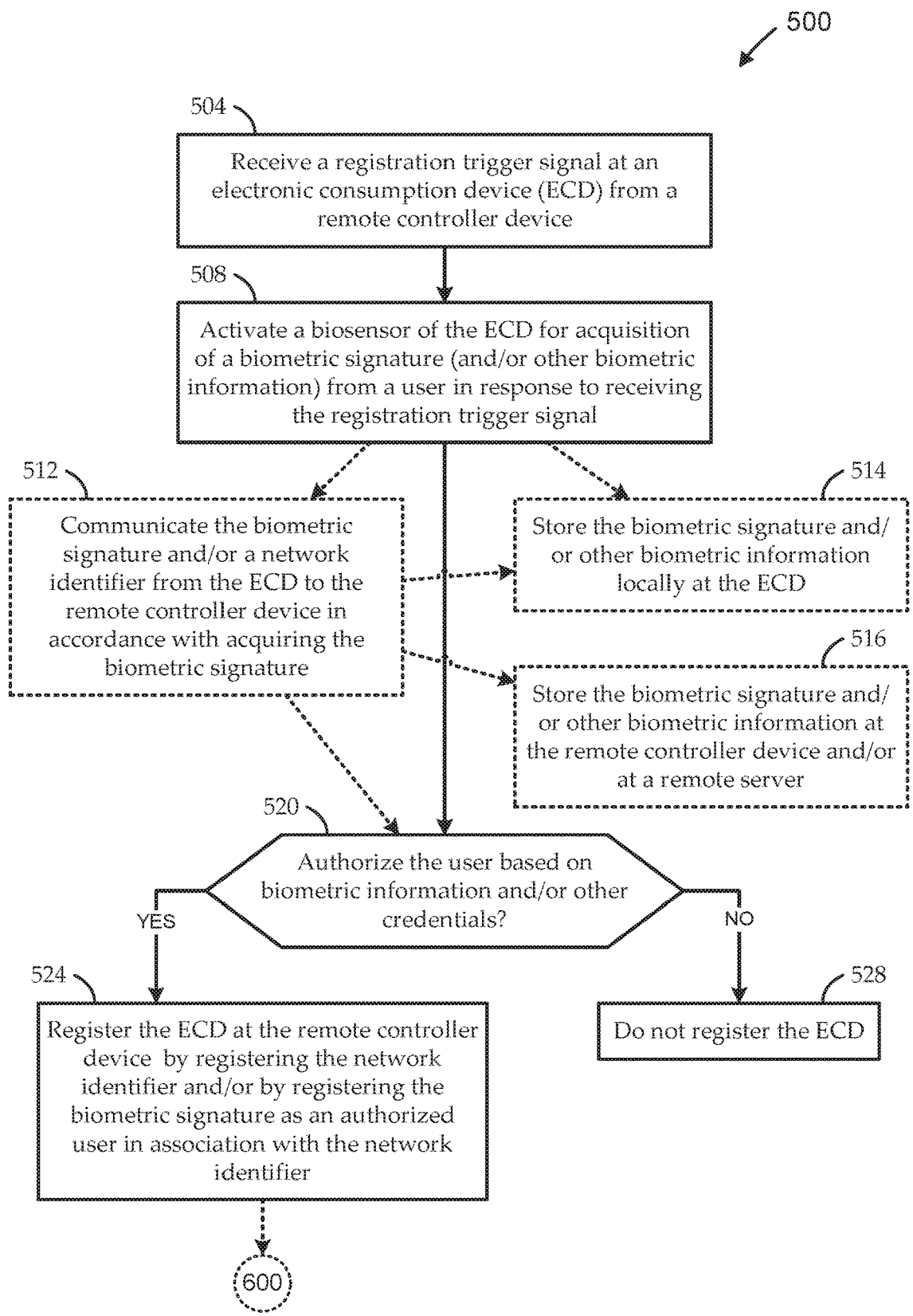
FIG. 5 shows a flow diagram of a method for registering a bio-traceable ECD, according to various embodiments.

FIG. 5 shows a flow diagram of a method 500 for registering a bio-traceable electronic consumable device (ECD), according to various embodiments. Embodiments of the method 500 begin at stage 504 by receiving a registration trigger signal at the ECD from a remote controller device via a network (e.g., a wireless communication network). At stage 508, embodiments can activate the biosensor for acquisition of the biometric signature (and/or other biometric information) from the user in response to receiving the registration trigger signal at stage 504. Having received the biometric signature (and/or other biometric information) from the user, embodiments can proceed in various ways. Some embodiments proceed, at stage 512, to communicate the biometric signature and/or a network identifier from the ECD to the remote controller device in accordance with acquiring the biometric signature. Additionally or alternatively, at stage 514, some embodiments store the biometric signature (and/or other biometric information) locally in memory of the ECD. Additionally or alternatively, at stage 514, some embodiments store the biometric signature (and/or other biometric information) remotely in memory of the remote controller device and/or of one or more remote servers (e.g., in cloud-based storage).

In some embodiments, it is assumed that the user from whom the biometric signature has been acquired is allowed to be an authorized user of the ECD. In other embodiments, at stage 520, the method 500 can determine whether to authorize the user based on the acquired biometric information and/or other credentials. For example, the acquired biometric information can be analyzed to see if it is sufficient for registration, the acquired biometric information can be analyzed to see if it matches an individual that is permitted to or restricted from registering the ECD, identification or other credentials of the user (e.g., a driver's license, biometric identification card, etc.) can be analyzed (e.g., automatically by the remote controller device, manually by a vendor of the ECD, etc.) to determine whether the user meets criteria for registering the ECD, etc. If the determination at stage 520 is not to authorize the user, embodiments can proceed at stage 528 by not registering the ECD. For example, the remote controller device and/or the ECD can indicate a registration failure using any suitable indication. If the determination at stage 520 is to authorize the user, embodiments can proceed at stage 524 by registering the ECD at the remote controller device. In some implementations, the registration involves by registering the network identifier at the remote controller device as a registered ECD. In other implementations, the registration involves registering the biometric signature as an authorized user in association with the network identifier at the remote controller device. Some embodiments, subsequent to successful registration at stage 524, can continue to the method 600 of FIG. 6.

Figure 6:
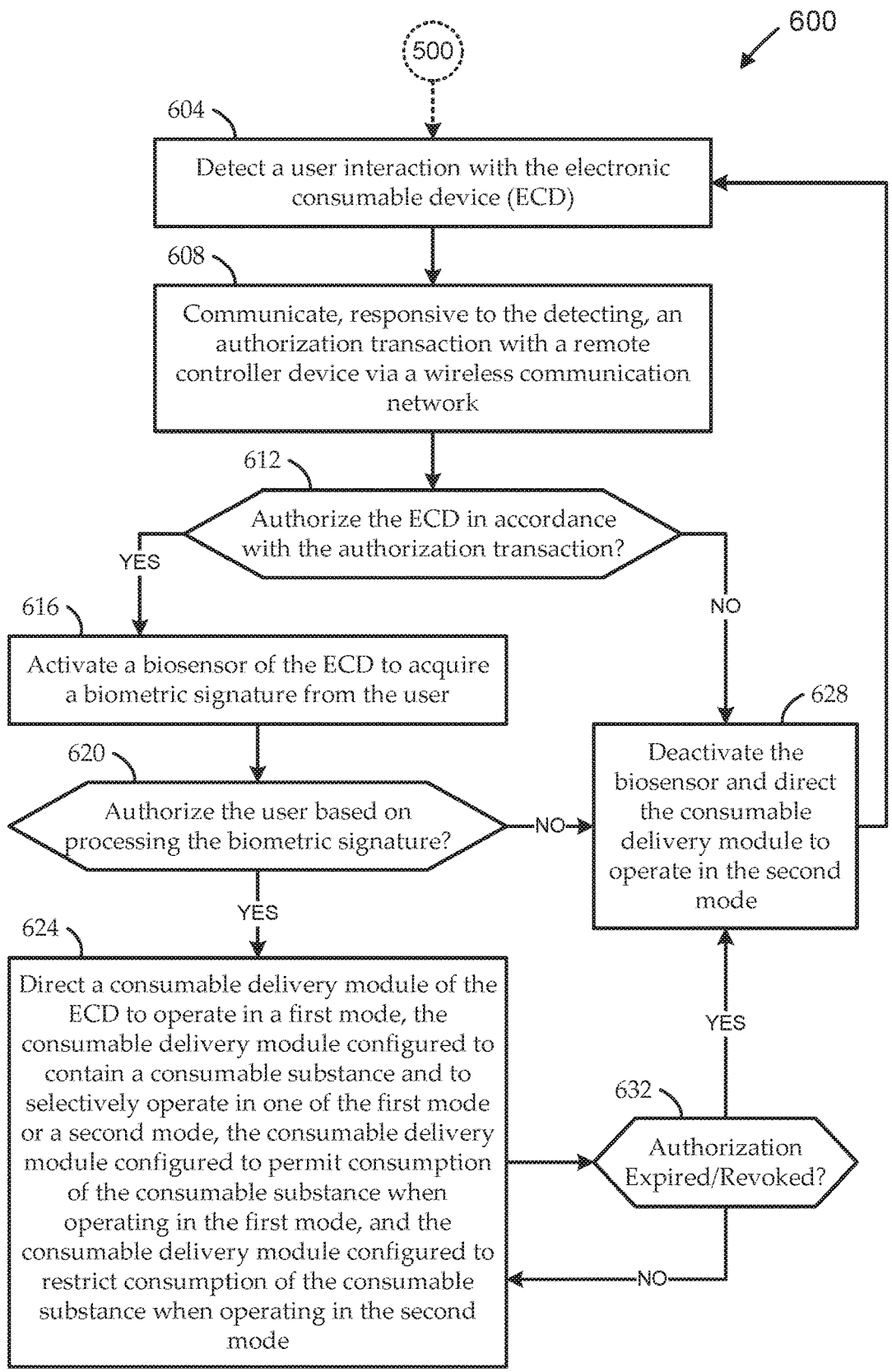
FIG. 6 shows a flow diagram of a method for using a bio-traceable ECD, according to various embodiments.

FIG. 6 shows a flow diagram of a method 600 for using a bio-traceable electronic consumable device (ECD), according to various embodiments. As illustrated, some embodiments of the method 600 flow from (e.g., are subsequent to) successful registration of the ECD in association with an authorized user, such as described with reference to the method 500 of FIG. 5. Embodiments of the method 600 can begin at stage 604 by detecting a user interaction with the ECD. At stage 608, embodiments can communicate, responsive to the detecting at stage 604, an authorization transaction with a remote controller device via a wireless communication network. At stage 612, embodiments can determine whether to authorize the ECD in accordance with the authorization transaction (i.e., whether to grant device-level authorization). If the device-level authorization at stage 612 fails, embodiment can deny usage of the ECD at stage 628. For example, embodiments can maintain one or more biosensors in a deactivated state (or deactivate the one or more biosensors, if presently in an activated state). Some embodiments can additionally or alternatively maintain a consumable delivery module of the ECD in a consumption-restrictive mode (or set the consumable delivery module of the ECD to the consumption-restrictive mode, if presently in a consumption-permissive mode). For example, the consumable delivery module is configured to contain a consumable substance and to selectively operate in one of the first mode or a second mode. In the first mode, the consumable delivery module is configured to permit consumption of the consumable substance; in the second mode, the consumable delivery module is configured to restrict consumption of the consumable sub stance.

If the determination at stage 612 is to authorize the ECD, embodiments can proceed at stage 616 to activate a biosensor of the ECD to acquire a biometric signature from the user. At stage 620, embodiments can determine whether to authorize the user based on processing the biometric signature (i.e., whether to grant user-level authorization). If the user-level authorization at stage 620 fails, embodiment can deny usage of the ECD at stage 628. For example, embodiments can deactivate the biosensor, and/or embodiments can maintain a consumable delivery module of the ECD in a consumption-restrictive mode (or set the consumable delivery module of the ECD to the consumption-restrictive mode, if presently in a consumption-permissive mode). If the determination at stage 620 is to authorize the user, embodiments can proceed at stage 624 to direct the consumable delivery module of the ECD to operate in the first (i.e., consumption-permissive) mode.

In some embodiments, at stage 632, after granting device-level authorization and user-level authorization, a continuous or periodic determination can be made as to whether the authorization has expired or been revoked. As one example, the granted authorization can be valid for some duration of time, after which device-level authorization and/or user-level authorization automatically expires. As another example, user-level authorization is repeatedly analyzed by repeatedly iterating stage 620 during usage of the ECD, and such authorization is automatically revoked when an iteration results in a failure to authorize the user. As another example, a particular event (e.g., not using the device for consumption for a duration of time) triggers revocation of the authorization. As another example, a remote controller device issues a command to revoke device-level authorization. In any of these and/or other cases, previously granted authorization becomes expired or revoked, and the method 600 can proceed to stage 628. For example, embodiments can deactivate the biosensor and/or set the consumable delivery module of the ECD to the consumption-restrictive mode.

While this disclosure contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

A recitation of "a", "an" or "the" is intended to mean "one or more" unless specifically indicated to the contrary.

Ranges may be expressed herein as from "about" one specified value, and/or to "about" another specified value. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. When such a range is expressed, another embodiment includes from the one specific value and/or to the other specified value. Similarly, when values are expressed as approximations, by use of the antecedent "about," it will be understood that the specified value forms another embodiment. It will be further understood that the endpoints of each of the ranges are included with the range.

All patents, patent applications, publications, and descriptions mentioned here are incorporated by reference in their entirety for all purposes. None is admitted to be prior art.

What is claimed is:

1. An electronic consumable device comprising:
    a consumable delivery module configured to contain a consumable substance and to selectively operate in one of a first mode or a second mode, the consumable delivery module configured to permit consumption of the consumable substance when operating in the first mode, and the consumable delivery module configured to restrict consumption of the consumable substance when operating in the second mode;
    a network module, configured to communicate with a remote controller device via a wireless communication network, the network module associated with a network identifier;
    an interface module comprising a biosensor to obtain a biometric signature from a user; and
    a central processor, coupled with the consumable delivery module, the network module, and the interface module, to:
        register the biometric signature at the remote controller device as an authorized user in association with the network identifier by directing the interface module, in accordance with receiving a registration trigger signal from the remote controller device, to activate the biosensor for acquisition of the biometric signature from the user and to communicate the network identifier and the biometric signature to the remote controller device;
        direct, subsequent to registering the biometric signature and responsive to detecting a user interaction via the interface module, the network module to communicate an authorization transaction with the remote controller device via the wireless communication network;
        determine whether to authorize the electronic consumable device in accordance with the authorization transaction; and
        in response to determining to authorize the electronic consumable device:
            direct the interface module to activate the biosensor for acquisition of the biometric signature from the user;
            process the biometric signature to determine whether to authorize the user; and
            direct the consumable delivery module to operate in the first mode in accordance with determining to authorize the user.

2. The electronic consumable device of claim 1, wherein the consumable delivery module comprises:
    an electronic vaporizer; and
    a receptacle for the consumable substance in thermal communication with the electronic vaporizer, such that, during operation of the consumable delivery module in the first mode, the electronic vaporizer is activatable to heat the consumable substance for delivery to the user.

3. The electronic consumable device of claim 1, further comprising:
    a memory,
    wherein the central processor is to register the biometric signature further by:
        directing storage of the biometric signature in the memory as associated with an authorized user.

4. The electronic consumable device of claim 1, wherein the central processor is to direct the network module to communicate the authorization transaction with the remote controller device via the wireless communication network by:
   directing the network module to communicate a device authorization request to the remote controller device via the wireless communication network; and
   receiving, by the network module from the remote controller device via the wireless communication network, responsive to the device authorization request, a device authorization response indicating whether to authorize the electronic consumable device.

5. The electronic consumable device of claim 1, wherein the central processor is to:
   direct the network module to communicate the authorization transaction by directing the network module to listen for a device authorization signal from the remote controller device via the wireless communication network; and
   determine whether to authorize the electronic consumable device in accordance with the device authorization signal.

6. The electronic consumable device of claim 5, wherein the central processor is to:
   determine whether to authorize the electronic consumable device in accordance with the device authorization signal by determining to authorize the electronic consumable device only when no device authorization signal is received while the network module is directed to listen for the device authorization signal.

7. The electronic consumable device of claim 1, wherein:
   the central processor is to direct the consumable delivery module to operate in the first mode in accordance with determining to authorize the user for a predetermined duration; and
   the central processor is further to direct the consumable delivery module subsequently to operate in the second mode upon elapsing of the predetermined duration.

8. The electronic consumable device of claim 1, wherein:
   the central processor is to direct the interface module to activate the biosensor for periodic acquisition of the biometric signature from the user according to a predetermined acquisition rate, the central processor to process the biometric signature to determine whether to authorize the user in accordance with each acquisition to obtain a sequence of authorization determinations over time;
   the central processor is to direct the consumable delivery module to operate in the first mode while the sequence of authorization determinations indicates to authorize the user; and
   the central processor is further to direct the consumable delivery module subsequently to operate in the second mode in response to the sequence of authorization determinations indicating not to authorize the user.

9. The electronic consumable device of claim 1, wherein the central processor is further to:
   direct the consumable delivery module to operate in the second mode in accordance with determining not to authorize the user.

10. The electronic consumable device of claim 9, wherein the central processor is further to:
    direct the network module to communicate an unauthorized access attempt signal to the remote controller device via the wireless communication network responsive to determining not to authorize the user.

11. The electronic consumable device of claim 1, wherein:
    the network module comprises a wireless antenna coupled with a network processor to communicate with the remote controller device via the wireless communication network.

12. A method for bio-tracing an electronic consumable device, the method comprising:
    registering a biometric signature at a remote controller device as an authorized user in association with a network identifier by directing an interface module, in accordance with receiving a registration trigger signal from the remote controller device, to activate a biosensor for acquisition of the biometric signature from the user and to communicate the network identifier and the biometric signature to the remote controller device;
    detecting a user interaction with the electronic consumable device subsequent to registering the biometric signature;
    communicating, responsive to the detecting, an authorization transaction with the remote controller device via a wireless communication network;
    determining whether to authorize the electronic consumable device in accordance with the authorization transaction; and
    in response to determining to authorize the electronic consumable device:
       activating the biosensor of the electronic consumable device to acquire the biometric signature from the user;
       processing the biometric signature to determine whether to authorize the user; and
       directing a consumable delivery module of the electronic consumable device to operate in a first mode in response to determining to authorize the user, the consumable delivery module configured to contain a consumable substance and to selectively operate in one of the first mode or a second mode, the consumable delivery module configured to permit consumption of the consumable substance when operating in the first mode, and the consumable delivery module configured to restrict consumption of the consumable substance when operating in the second mode.

13. The method of claim 12, wherein the consumable delivery module comprises:
    an electronic vaporizer; and
    the directing the consumable delivery module to operate in the first mode comprises activating the electronic vaporizer to heat the consumable substance for delivery to the user.

14. The method of claim 12, wherein the registering further comprises:
    storing the biometric signature local to the electronic consumable device as associated with an authorized user.

15. The method of claim 12, wherein the communicating the authorization transaction with the remote controller device via the wireless communication network comprises:
    communicating a device authorization request to the remote controller device via the wireless communication network; and
    receiving, from the remote controller device via the wireless communication network, responsive to the device authorization request, a device authorization response indicating whether to authorize the electronic consumable device.

16. The method of claim 12, wherein:
    the communicating the authorization transaction with the remote controller device via the wireless communication network comprises configuring the electronic consumable device to listen for a device authorization signal from the remote controller device via the wireless communication network; and the determining whether to authorize the electronic consumable device is in accordance with the device authorization signal.

17. The method of claim 12, wherein the directing the consumable delivery module to operate in the first mode comprises:

directing the consumable delivery module to operate in the first mode for a predetermined duration; and directing the consumable delivery module to operate in the second mode upon elapsing of the predetermined duration.

18. The method of claim 12, further comprising:

directing the consumable delivery module to operate in the second mode in response to determining not to authorize the user.

19. An electronic consumable device comprising:

a central processor; and a memory having instructions stored thereon, which, when executed, cause the processor to:

register a biometric signature at a remote controller device as an authorized user in association with a network identifier by directing an interface module, in accordance with receiving a registration trigger signal from the remote controller device, to activate a biosensor for acquisition of the biometric signature from a user and to communicate the network identifier and the biometric signature to the remote controller device;

detect a user interaction with the electronic consumable device subsequent to registering the biometric signature;

communicate, responsive to the detecting, an authorization transaction with the remote controller device via a wireless communication network;

determine whether to authorize the electronic consumable device in accordance with the authorization transaction; and in response to determining to authorize the electronic consumable device:

activate the biosensor of the electronic consumable device to acquire the biometric signature from the user;

process the biometric signature to determine whether to authorize the user; and direct a consumable delivery module of the electronic consumable device to operate in a first mode in response to determining to authorize the user, the consumable delivery module configured to contain a consumable substance and to selectively operate in one of the first mode or a second mode, the consumable delivery module configured to permit consumption of the consumable substance when operating in the first mode, and the consumable delivery module configured to restrict consumption of the consumable substance when operating in the second mode.

* * * * *